United States Patent
Kumar et al.

(10) Patent No.: US 11,096,625 B2
(45) Date of Patent: Aug. 24, 2021

(54) SYSTEM AND METHOD OF DETERMINING SOBRIETY LEVELS

(71) Applicants: Deeptaanshu Kumar, Germantown, MD (US); Ajmal Thanikkal, Edgewood, PA (US); Prithvi Krishnamurthy, Bangalore (IN); Pei Zhang, Mountain View, CA (US); Xinlei Chen, Shanghai (CN)

(72) Inventors: Deeptaanshu Kumar, Germantown, MD (US); Ajmal Thanikkal, Edgewood, PA (US); Prithvi Krishnamurthy, Bangalore (IN); Pei Zhang, Mountain View, CA (US); Xinlei Chen, Shanghai (CN)

( * ) Notice: Subject to any disclaimer, the term of this patent is extended or adjusted under 35 U.S.C. 154(b) by 0 days.

(21) Appl. No.: 16/272,070

(22) Filed: Feb. 11, 2019

(65) Prior Publication Data
US 2020/0253549 A1    Aug. 13, 2020

(51) Int. Cl.
*A61B 5/00* (2006.01)
*A61B 5/11* (2006.01)

(52) U.S. Cl.
CPC .......... *A61B 5/4845* (2013.01); *A61B 5/1116* (2013.01); *A61B 5/1118* (2013.01); *A61B 5/0002* (2013.01); *A61B 5/1126* (2013.01)

(58) Field of Classification Search
CPC ... A61B 5/4845; A61B 5/1118; A61B 5/1116; A61B 5/1126; A61B 5/0002; A61B 5/6898
See application file for complete search history.

(56) References Cited

U.S. PATENT DOCUMENTS

| | | | |
|---|---|---|---|
| 2008/0228365 A1* | 9/2008 | White | B60R 25/257 701/70 |
| 2012/0065915 A1* | 3/2012 | Hara | G01M 1/122 702/96 |
| 2012/0112879 A1* | 5/2012 | Ekchian | B60K 28/063 340/5.53 |
| 2014/0311215 A1* | 10/2014 | Keays | A61B 5/082 73/23.3 |
| 2014/0313303 A1* | 10/2014 | Davis | A61B 5/0077 348/77 |
| 2015/0257681 A1* | 9/2015 | Shuster | A61B 5/18 600/301 |
| 2018/0284100 A1* | 10/2018 | Agu | G01N 33/4972 |
| 2019/0095814 A1* | 3/2019 | Dubovsky | A61B 5/1126 |

* cited by examiner

*Primary Examiner* — Gary Jackson
*Assistant Examiner* — Sebastian X Lukjan
(74) *Attorney, Agent, or Firm* — Dunlap Bennett & Ludwig, PLLC; Brendan E. Squire

(57) ABSTRACT

A system and method of detecting a sobriety of a subject utilizing a mobile device. The mobile device includes a processor and a memory storing historical data including movements indicating a drunk state, movements indicating a sober state, or a combination of both. The mobile device further includes a user interface, a recorder operable to capture a recording, and an accelerometer operable to generate acceleration values of movements of the recording. When the mobile device captures the recording of a subject performing movements, the processor compares the data on the memory with the acceleration values of the movements of the subject and produces an indication of either a drunk state of the subject or a sober state of the subject on the user interface.

12 Claims, 2 Drawing Sheets

SYSTEM AND METHOD OF DETERMINING SOBRIETY LEVELS

BACKGROUND OF THE INVENTION

The present invention relates to a system and method of determining sobriety levels.

Alcohol misuse is responsible for staggering amounts of personal and economic harm in the United States and abroad. Upwards of 88,000 people die from alcohol related issues each year, making it the third leading preventable cause of death in the United States. Excessive drinking has been linked to damage to the heart, liver, pancreas and immune system. In addition to the detrimental health effects, alcohol misuse cost the U.S. $223.5 billion in economic loss in 2006 alone. Binge drinking or drinking heavily over longer periods of time can have very serious consequences. Alcohol misuse not only harms the individual, but damages relationships and society in general in terms of violence and crime, accidents and drink driving. Thus, it is essential to have a low cost and easy-to-use personal device to detect people's drunk state.

Several different methods are available for testing intoxication. A test can be done via blood draw, breath (breathalyzer), urine or saliva, and recent hairs. All of these methods directly attempt to measure the physical presence of alcohol. In contrast, field sobriety tests performed by police officers often use physical tasks to gauge an individual's level of impairment. The Standardized Field Sobriety test uses three measures for determining sobriety: Horizontal Gaze Nystagmus, Walk-and-Turn, and One-Leg Stand. The evidential breath testing devices are generally expensive (costs range from $3000-$5000 per unit), require routine calibration maintenance, and costly repairs. Calibration, and operation of this class of devices require specially trained and certified personnel. In addition, since the same level of BAC can affect people differently, an individual may pass a breathalyzer but still be impaired.

As can be seen, there is a need for a cost effective and convenient system and method of determining sobriety levels.

SUMMARY OF THE INVENTION

In one aspect of the present invention, a system of detecting a sobriety of a subject comprises: a mobile device comprising: a processor; a memory storing data comprising at least one of movements indicating a drunk state and movements indicating a sober state; a user interface; a recorder operable to capture a recording; an accelerometer operable to generate acceleration values of movements of the recording, wherein when the mobile device captures the recording of a subject performing movements, the processor compares the data on the memory with the acceleration values of the movements of the subject; and produces an indication of either a drunk state of the subject or a sober state of the subject on the user interface.

In another aspect of the present invention, a method of detecting a sobriety of a subject comprises: capturing, via a recorder of a mobile device, movements of the subject; generating, via an accelerometer of the mobile device, acceleration values of the movements of the subject; comparing, via software running on a computer, the acceleration values of the subject with saved data comprising at least one of movements indicating a drunk state and movements indicating a sober state; and producing, via a user interface of the mobile device, an indication of the either the drunk state or the sober state of the subject.

These and other features, aspects and advantages of the present invention will become better understood with reference to the following drawings, description and claims.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

The present invention includes a system and method for determining sobriety level by analyzing physical movements of the user. The present invention captures and analyzes sensor data on a mobile device to determine the drunk state of a person. Drunk subjects have a certain pattern in signals, which can be used to determine the drunk state. The present invention has a custom data classifier that can determine if this pattern is evident in the sensing data and provides the result back to the users.

The present invention is both cost-effective and easy-to-use. The present invention may only utilize general sensors on mobile devices working with a custom classifier to give accurate measurements across gender/physical body types, which allows for zero cost on additional hardware. During the test, subjects only need to follow very simple activities, which gives the average person the ability to use the present invention without specialized training. At a technical level, the present invention extracts temporal and frequency domain features of a signal collected from a subject, and therefore provides a more quantitative measure of the drunkenness as compared to the two physical activity parts of the standardized test, Walk-and-Turn, and One-Leg Stand.

Figure 1:
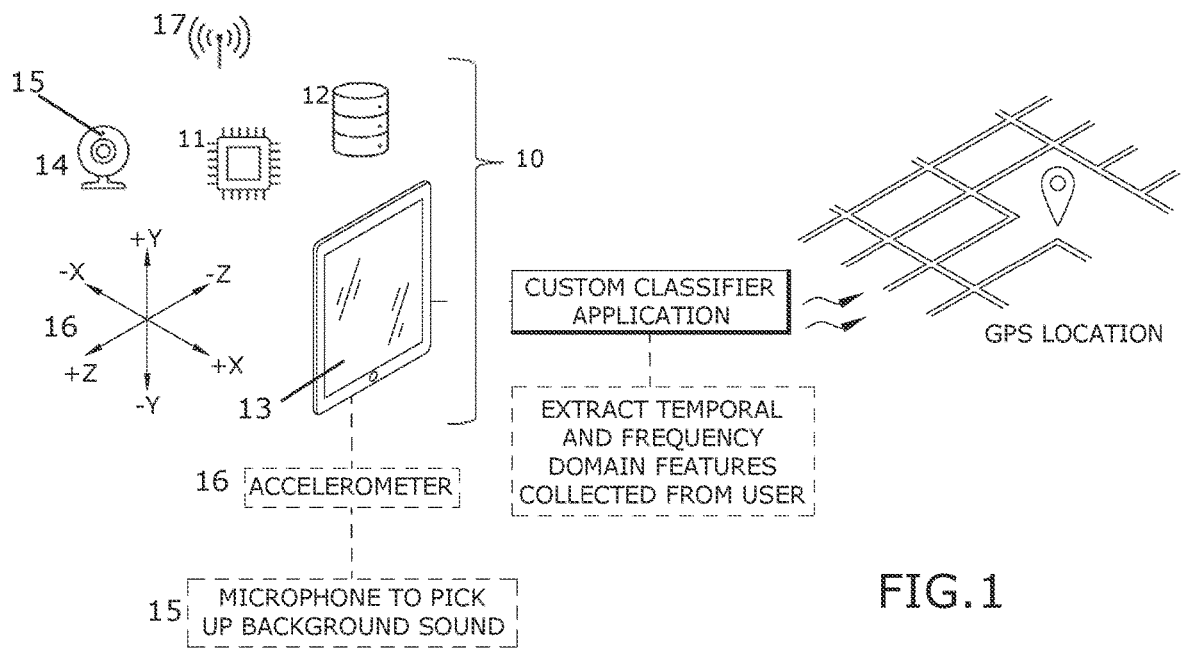
FIG. 1 is a schematic view of an embodiment of the present invention.
Figure 2:
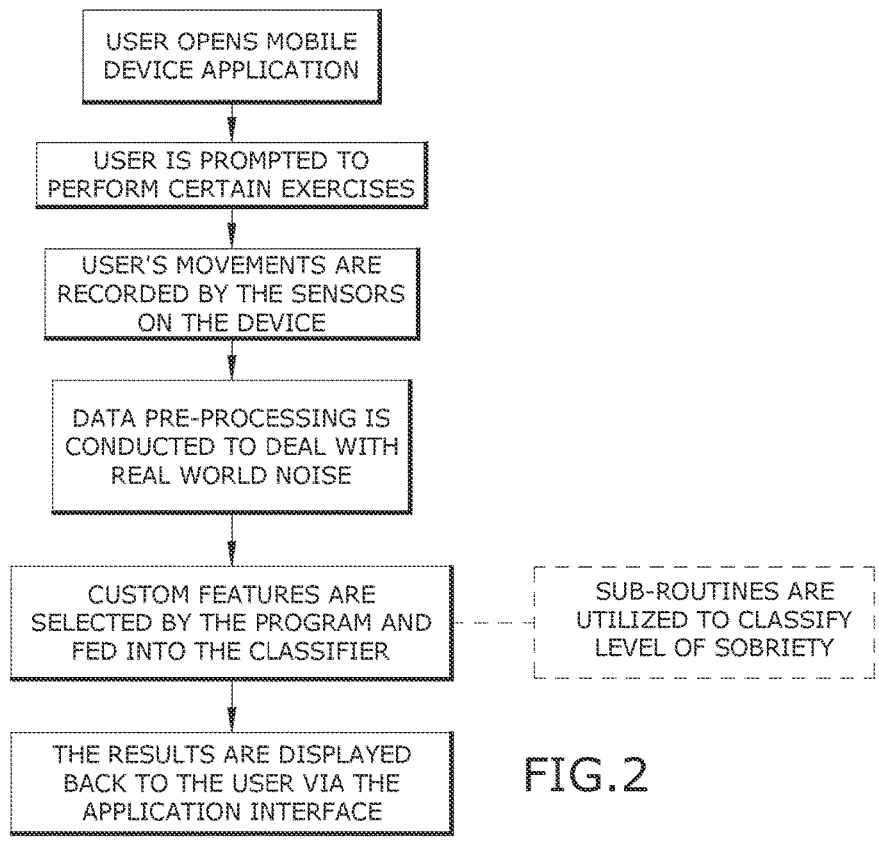
FIG. 2 is a flow chart of an operational flow of an embodiment of the present invention.
Figure 3:
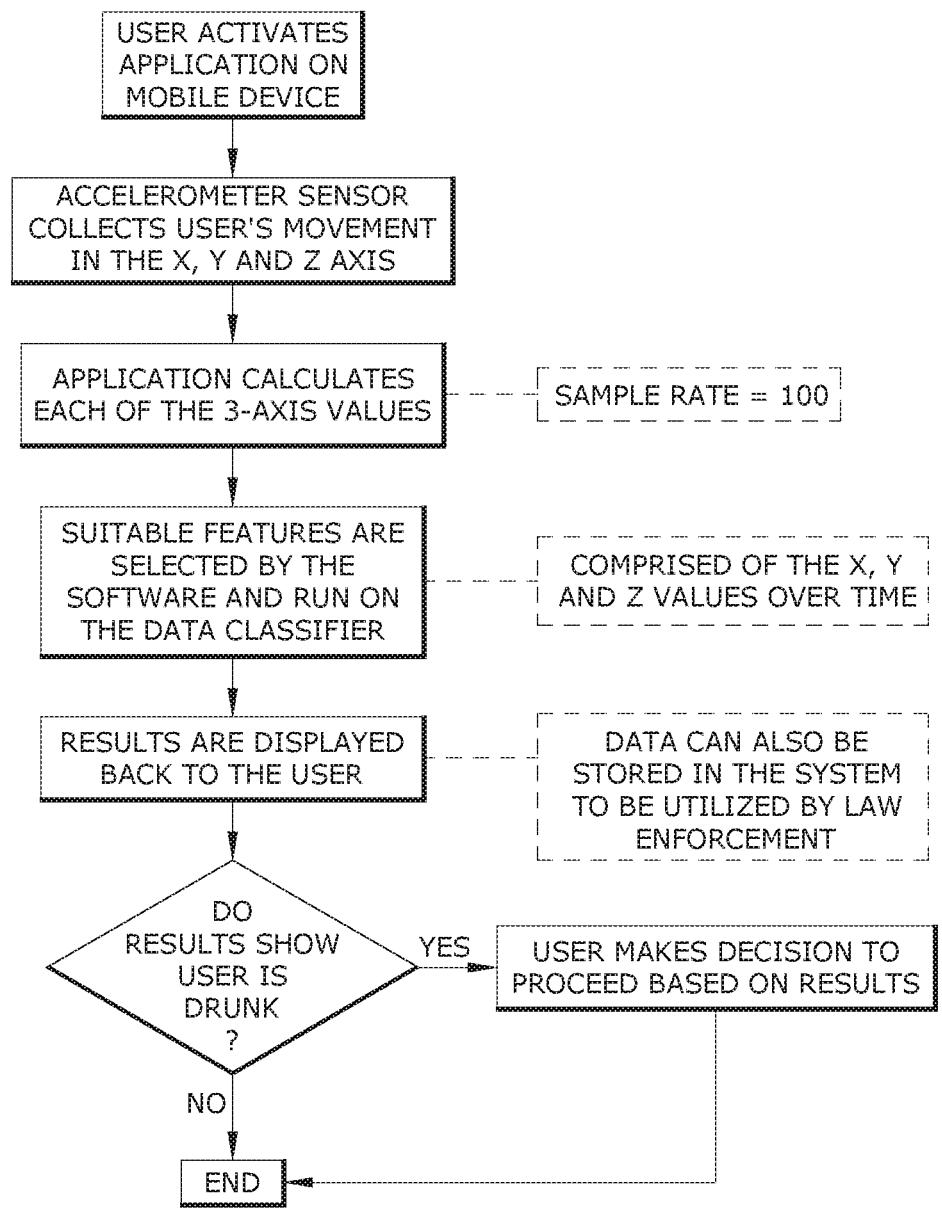
FIG. 3 is a flow chart of a user interface of an embodiment of the present invention.

Referring to FIGS. 1 through 3, the present invention includes a system and method of detecting a sobriety of a subject utilizing a mobile device 10. The mobile device 10 includes a processor 11 and a memory 12 storing historical data including movements indicating a drunk state, movements indicating a sober state, or a combination of both. The mobile device 10 further includes a user interface 13, a recorder 14 operable to capture a recording, the recorder 14 may also include a microphone 15, and an accelerometer 16 operable to generate acceleration values of movements of the recording. When the mobile device 10 captures the recording of a subject performing movements, the processor 11 compares the data on a memory 12 with the acceleration values of the movements of the subject and produces an indication of either a drunk state of the subject or a sober state of the subject on the user interface 13.

The mobile device of the present invention may include a smart phone, a tablet, or another handheld device with a computing system. The computing system is at least the processor and the memory. The computing system may execute on any suitable operating system such as IBM's zSeries/Operating System (z/OS), MS-DOS, PC-DOS, MAC-iOS, WINDOWS, UNIX, OpenVMS, ANDROID, an operating system based on LINUX, or any other appropriate operating system, including future operating systems.

In particular embodiments, the computing system 10 includes a processor 11, memory 12, a user interface 13, and a communication interface 17. In particular embodiments, the processor 11 includes hardware for executing instructions, such as those making up a computer program. The memory 12 includes main memory for storing instructions such as computer program(s) for the processor 11 to execute, or data for processor 11 to operate on. The memory 12 may include a hard disk drive (HDD), a floppy disk drive, flash memory, an optical disc, a magneto-optical disc, magnetic tape, a Universal Serial Bus (USB) drive, a solid-state drive (SSD), or a combination of two or more of these. The memory 12 may include removable or non-removable (or fixed) media, where appropriate. The memory 12 may be internal or external to computing system, where appropriate. In particular embodiments, the memory 12 is non-volatile, solid-state memory.

The user interface includes hardware, software, or both providing one or more interfaces for user communication with the computing system. As an example and not by way of limitation, the user interface may include a keyboard, keypad, microphone, monitor, mouse, printer, scanner, speaker, still camera, stylus, tablet, touchscreen, trackball, video camera, another user interface or a combination of two or more of these.

The communication interface includes hardware, software, or both providing one or more interfaces for communication (e.g., packet-based communication) between the computing system and one or more other computing systems or one or more networks. As an example, and not by way of limitation, communication interface may include a network interface controller (NIC) or network adapter for communicating with an Ethernet or other wire-based network or a wireless NIC (WNIC) or wireless adapter for communicating with a wireless network, such as a WI-FI network. This disclosure contemplates any suitable network and any suitable communication interface. As an example, and not by way of limitation, the computing system may communicate with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, the computing system may communicate with a wireless PAN (WPAN) (e.g., a BLUETOOTH WPAN), a WI-FI network, a WI-MAX network, a cellular telephone network (e.g., a Global System for Mobile Communications (GSM) network), or other suitable wireless network or a combination of two or more of these. The computing system may include any suitable communication interface for any of these networks, where appropriate.

As mentioned above, the present invention may be implemented on a smartphone or other mobile devices. The user may either download an application online or the present invention may be pre-loaded on a dedicated device. The historical saved data including the movements indicating the drunk state and movements indicating the sober state may be locally saved on the mobile device or remotely stored and wirelessly accessed from a database. The historical saved data may be considered a drunk state classifier which includes a model based on a large sample of historical data.

The movements of the subject are recorded in real time by the sensors on the mobile device 10. The movements may be produced by different activities such as exercise, speech, eye movement, and the like. A data pre-process is conducted to deal with noise from the physical world. This pre-process isolates the data generated by the movement of the person rather than external factors such as wind, extreme weather, etc. The subject's movements and acceleration are calculated in the x, y, and z-axis. The processor then identifies the right features to feed into the drunk state classifier. The drunk state classifier includes the historical data, which includes of the x-axis, y-axis, and z-axis values over time of the movements indicating the drunk state, the movements indicating the sober state, or both. Results are produced if the data matches more closely with that of the sober or non-sober individuals. Results are then displayed back to the user on the mobile devices' user-interface informing the user if the user is sober or drunk.

In alternate embodiments, optional sensors could be used to help the classifier. For example, global position system (GPS) location information can detect if users have been near any bars or places that serve alcohol. The GPS feature may also assist police and other law enforcement to locate individuals who have failed the sobriety test of the present invention and are driving a vehicle while drunk. Another example is to apply a microphone to detect the background sound to imply a drinking environment. These extra sensor data could be fused with the accelerometer data to help detect a drunk state.

It should be understood, of course, that the foregoing relates to exemplary embodiments of the invention and that modifications may be made without departing from the spirit and scope of the invention as set forth in the following claims.

What is claimed is:

1. A system of detecting a sobriety of a subject comprising:
   a mobile device comprising:
      a processor;
      a non-volatile memory storing historical data comprising at least one of movements of one or more subjects indicating a drunk state and movements of one or more subjects indicating a sober state; a user interface;
      a recorder operable to capture a recording of an individual subject performing a real time movement;
      an accelerometer operable to generate acceleration values of the real time movement, the acceleration values captured with the recording, wherein
      when the mobile device captures the recording of the acceleration values of the individual subject performing the real time movement,
      the processor performs pre-processing to isolate the acceleration values of the subject from one of a plurality of external factors to eliminate an acceleration noise from the acceleration values of the individual subject to provide isolated acceleration values;
      a drunk state classifier provides a model based on the historical data on the memory comprising x-axis, v-axis, and z-axis acceleration values over time of the at least one of the movements indicating the drunk state and the movements indicating the sober state;
      the drunk state classifier extracts a temporal domain feature and a frequency domain feature of the isolated acceleration values of the subject and compares the data on the memory with the isolated acceleration values of the movements of the individual subject; and the drunk state classifier produces an indication of either a drunk state of the individual subject or a sober state of the individual subject on the user interface.

2. The system of claim 1, wherein the processor calculates each of x-axis, y-axis, and z-axis acceleration values of the subject's real time movement; and identifies movements of the subject to feed to the drunk state classifier to compare with the historical data on the memory.

3. The system of claim 1, wherein the movement is at least one of an exercise, speech, and eye movement.

4. The system of claim 1, wherein the recorder is a camera and microphone.

5. The system of claim 1, wherein the user interface is a touchscreen, and the indication is produced on the touchscreen.

6. The system of claim 1, wherein the mobile device further comprises a telecommunications module.

7. A method of detecting a sobriety of a subject comprising:

capturing, via a recorder of a mobile device, one or more movements of the subject;

generating, via an accelerometer of the mobile device, an acceleration values of the one or more movements of the subject in each of an X-axis, a v-axis; and a z-axis;

isolating, via a processor, the acceleration values of the one or more movements of the subject from a plurality of external factors to eliminate an acceleration noise from the acceleration values;

modeling, via a drunk state classifier, historical data of one or more subjects stored on a non-transient memory, the historical data comprising x-axis, y-axis, and z-axis acceleration values over time of at least one of a historical movement indicating a drunk state and a historical movement indicating a sober state;

extracting, via the drunk state classifier, a temporal domain feature and a frequency domain feature of the isolated acceleration values of the subject;

comparing, via software running on a computer, the isolated acceleration values of the subject with the historical data comprising at least one of the historical movements indicating a drunk state and the historical movements indicating a sober state; and producing, via a user interface of the mobile device, an indication of the either the drunk state or the sober state of the subject.

8. The method of claim 7, further comprising calculating, via software running on the computer, each of x-axis, y-axis, and z-axis acceleration values of the subject's movements; and identifying movements of the subject to compare with the saved data.

9. The method of claim 7, wherein the one or movements is at least one of an exercise, speech, and eye movement.

10. The method of claim 7, wherein the recorder is a camera and microphone.

11. The method of claim 7, wherein the user interface is a touchscreen, and the indication is produced on the touchscreen.

12. The method of claim 7, wherein the mobile device further comprises a telecommunications module.

* * * * *